(12) United States Patent
Müller et al.

(10) Patent No.: US 6,200,931 B1
(45) Date of Patent: Mar. 13, 2001

(54) 5,6-DIHYDRO-(1,4,2)-DIOXAZIN-SUBSTITUTED (HETERO) ARYL-(OXY-, IMINO-, ALKYL-)-SULPHONYLAMINO (THIO)CARBONYL-HETEROCYCLYL DERIVATIVES, THEIR PREPARATION AND THEIR USE AS HERBICIDES

(75) Inventors: Klaus-Helmut Müller, Düsseldorf; Mark Wilhelm Drewes, Langenfeld; Kurt Findeisen, Leverkusen; Ernst Rudolf F. Gesing, Erkrath-Hochdahl; Johannes Rudolf Jansen; Rolf Kirsten, both of Monheim; Joachim Kluth, Langenfeld; Ulrich Philipp, Köln; Hans-Jochem Riebel, Wuppertal; Klaus König, Odenthal, all of (DE); Markus Dollinger, Overland Park, KS (US); Hans-Joachim Santel, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/242,253

(22) PCT Filed: Aug. 4, 1997

(86) PCT No.: PCT/EP97/04233

§ 371 Date: May 13, 1999

§ 102(e) Date: May 13, 1999

(87) PCT Pub. No.: WO98/07721

PCT Pub. Date: Feb. 26, 1998

(30) Foreign Application Priority Data

Aug. 16, 1996 (DE) .............................................. 196 32 945

(51) Int. Cl.$^7$ ....................... A01N 43/88; C07D 413/04; C07D 413/12; C07D 413/14

(52) U.S. Cl. ............................................. 504/223; 544/65

(58) Field of Search ................ 544/65; 504/223

(56) References Cited

U.S. PATENT DOCUMENTS

| | | | |
|---|---|---|---|
| 3,769,282 | 10/1973 | Omodei-Sale et al. | 260/244 R |
| 5,057,144 | 10/1991 | Daum et al. | 71/92 |
| 5,085,684 | 2/1992 | Muller et al. | 71/92 |
| 5,094,683 | 3/1992 | Daum et al. | 71/94 |
| 5,149,356 | 9/1992 | Muller et al. | 71/90 |
| 5,205,853 | 4/1993 | Wolf et al. | 504/247 |
| 5,238,910 | 8/1993 | Muller et al. | 504/273 |
| 5,241,074 | 8/1993 | Daum et al. | 548/263.8 |
| 5,252,540 | 10/1993 | Heistracher et al. | 504/280 |
| 5,256,632 | 10/1993 | Wolf et al. | 504/252 |
| 5,276,162 | 1/1994 | Muller et al. | 548/263.4 |
| 5,300,480 | 4/1994 | Haas et al. | 504/273 |
| 5,380,863 | 1/1995 | Muller et al. | 548/263.6 |
| 5,405,970 | 4/1995 | Daum et al. | 548/263.6 |
| 5,476,936 | 12/1995 | Philipp et al. | 504/223 |
| 5,488,028 | 1/1996 | Haas et al. | 504/193 |
| 5,532,378 | 7/1996 | Daum et al. | 548/263.8 |
| 5,534,486 | 7/1996 | Muller et al. | 504/273 |
| 5,541,337 | 7/1996 | Muller et al. | 548/263.6 |
| 5,552,369 | 9/1996 | Findeisen et al. | 504/273 |
| 5,554,761 | 9/1996 | Haas et al. | 548/263.6 |
| 5,580,842 | 12/1996 | Philipp et al. | 504/213 |
| 5,597,939 | 1/1997 | Muller et al. | 558/8 |
| 5,599,944 | 2/1997 | Muller et al. | 548/263.6 |
| 5,625,074 | 4/1997 | Daum et al. | 548/263.8 |
| 5,631,380 | 5/1997 | Haas et al. | 548/263.4 |
| 5,652,372 | 7/1997 | Muller et al. | 548/263.4 |
| 5,654,438 | 8/1997 | Findeisen et al. | 548/263.8 |
| 5,750,718 | 5/1998 | Muller et al. | 548/263.6 |

OTHER PUBLICATIONS

Chemical Abstracts, vol. 114, No. 9, Mar. 4, 1991, Abstract No. 77044x.

*Primary Examiner*—Richard L. Raymond
(74) *Attorney, Agent, or Firm*—Joseph C. Gil

(57) ABSTRACT

The invention relates to novel substituted sulphonylamino (thio)carbonyl compounds of the formula (I)

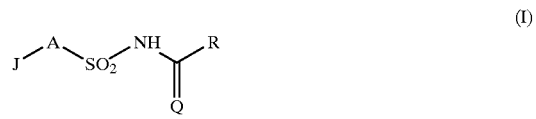

in which

A represents a single bond, represents oxygen, imino (NH), alkanediyl (alkylene) or alkylimino (N-alkyl), J represents a (hetero)aryl grouping selected from the series phenyl, pyridyl, pyrazolyl, thienyl which is substituted by a 5,6-dihydro-[1,4,2]-dioxazin-3-yl group (which may for its part be substituted by halogen, alkyl or halogenoalkyl) and optionally by one or two further radicals selected from the series cyano, halogeno, alkyl, halogenoalkyl, phenyl, pyridyl, Q represents oxygen or sulphur and, R represents optionally substituted heterocyclyl having 5 ring members of which at least one is oxygen, sulphur or nitrogen and one to three more may be nitrogen, and salts of compounds of the formula (I), processes and specific novel intermediates for their preparation and their use as herbicides.

11 Claims, No Drawings

5,6-DIHYDRO-(1,4,2)-DIOXAZIN-SUBSTITUTED (HETERO) ARYL-(OXY-, IMINO-, ALKYL-)-SULPHONYLAMINO (THIO)CARBONYL-HETEROCYCLYL DERIVATIVES, THEIR PREPARATION AND THEIR USE AS HERBICIDES

This aplication is a 371 of PCT/EP97/04233, filed Aug. 4, 1997.

TECHNICAL FIELD OF THE INVENTION

The invention relates to novel substituted sulphonylamino (thio)carbonyl compounds, to a plurality of processes for their preparation and to their use as herbicides.

BACKGROUND OF THE INVENTION

It is known that certain substituted sulphonylamino(thio) carbonyl compounds have herbicidal properties (cf. EP 341 489, EP 422 469, EP 425 948, EP 431 291, EP 507 171, EP 534 266, EP 569 810, DE 40 29 753). However, the activity of these compounds is not satisfactory in every respect.

DETAILED DESCRIPTION OF THE INVENTION

This invention, accordingly, provides novel substituted sulphonylamino(thio)carbonyl compounds of the general formula (I)

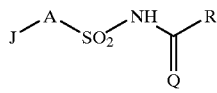

(I)

in which
  A represents a single bond, represents oxygen, imino (NH), alkanediyl (alkylene) or alkylimino (N-alkyl),
  J represents a (hetero)aryl grouping selected from the series phenyl, pyridyl, pyrazolyl, thienyl which is substituted by a 5,6-dihydro-[1,4,2]-dioxazin-3-yl group (which may for its part be substituted by halogen, alkyl or halogenoalkyl) and optionally by one or two further radicals selected from the series cyano, halogeno, alkyl, halogenoalkyl, phenyl, pyridyl,
  Q represents oxygen or sulphur and,
  R represents optionally substituted heterocyclyl having 5 ring members of which at least one is oxygen, sulphur or nitrogen and one to three more may be nitrogen,
and salts of compounds of the formula (I).

The novel substituted sulphonylamino(thio)carbonyl compounds of the general formula (I) are obtained when (a) aminosulphonyl compounds of the general formula (II)

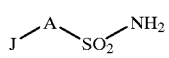

(II)

in which
  A and J are each as defined above
  are reacted with (thio)carboxylic acid derivatives of the general formula (III)

(III)

in which
  Q and R are each as defined above and
  Z represents halogen, alkoxy, aryloxy or arylalkoxy,
    if appropriate in the presence of an acid acceptor and
    if appropriate in the presence of a diluent,
or when (b) sulphonyl iso(thio)cyanates of the general formula (IV)

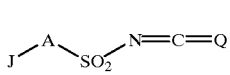

(IV)

in which
  A, J and Q are each as defined above
  are reacted with heterocycles of the general formula (V)

(V)

in which
  R is as defined above,
    if appropriate in the presence of a reaction auxiliary
    and if appropriate in the presence of a diluent,
or when (c) chlorosulphonyl compounds of the general formula (VI)

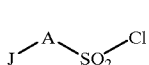

(VI)

in which
  A and J are each as defined above
  are reacted with heterocycles of the general formula (V)

(V)

in which
  R is as defined above
  and metal (thio)cyanates of the general formula (VII)

MQCN            (VII)

in which
  Q is as defined above and
  M represents an alkali metal or alkaline earth metal equivalent,
    if appropriate in the presence of a reaction auxiliary and if appropriate in the presence of a diluent,
or when (d) chlorosulphonyl compounds of the general formula (VI)

(VI)

in which
A and J are each as defined above
are reacted with (thio)carboxamides of the general formula (VIII)

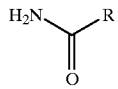
(VIII)

in which
Q and R are each as defined above,
if appropriate in the presence of an acid acceptor and
if appropriate in the presence of a diluent, or when (e) sulphonylamino(thio)carbonyl compounds of the general formula (IX)

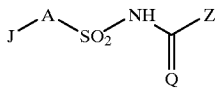
(IX)

in which
A, J and Q are each as defined above and
Z represents halogen, alkoxy, aryloxy or arylalkoxy
are reacted with heterocycles of the general formula (V)

H—R  (V)

in which
R is as defined above,
if appropriate in the presence of an acid acceptor and
if appropriate in the presence of a diluent, or when (f) heterocycles of the general formula (V)

H—R  (V)

in which
R is as defined above
are reacted with chlorosulphonyl iso(thio)cyanate, if appropriate in the presence of a diluent, and the adducts, formed in the process, of the general formula (X)

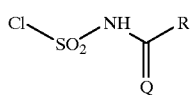
(X)

in which
Q and R are each as defined above
are reacted in situ with (hetero)aryl compounds of the general formula (XI)

(XI)

in which
A and J are each as defined above,
if appropriate in the presence of an acid acceptor
and if appropriate in the presence of a diluent,
and the compounds of the formula (I) obtained by the processes (a), (b), (c), (d), (e) or (f) are, if appropriate, converted into salts by customary methods.

The novel substituted sulphonylamino(thio)carbonyl compounds of the general formula (I) have strong herbicidal activity.

The invention preferably provides compounds of the formula (I) in which

A represents a single bond, represents oxygen, imino (NH), $C_1$–$C_4$-alkanediyl or $C_1$–$C_4$-alkylimino, J represents a (hetero)aryl grouping selected from the series phenyl, pyridyl, pyrazolyl, thienyl which is substituted by a 5,6-dihydro-[1,4,2]-dioxazin-3-yl group (which may for its part be substituted by halogen, $C_1$–$C_4$-alkyl or $C_1$–$C_4$-halogenoalkyl) and optionally by one or two further radicals selected from the series cyano, halogen, $C_1$–$C_4$-alkyl, $C_1$–$C_4$-halogenoalkyl, phenyl, pyridyl, Q represents oxygen or sulphur and R represents heterocyclyl of the formulae below, each of which is optionally substituted,

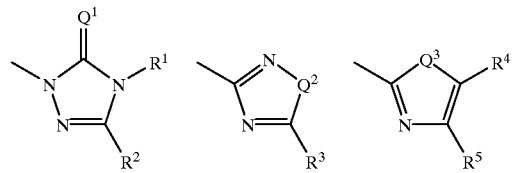

in which $Q^1$, $Q^2$ and $Q^3$ each represent oxygen or sulphur and $R^1$ represents hydrogen, hydroxyl, amino, cyano, represents $C_2$–$C_{10}$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents $C_2$–$C_6$-alkenyl or $C_2$–$C_6$-alkinyl, each of which is optionally substituted by fluorine, chlorine and/or bromine, represents $C_1$–$C_6$-alkoxy, $C_1$–$C_6$-alkylamino or $C_1$–$C_6$-alkyl-carbonylamino, each of which is optionally substituted by fluorine, chlorine, bromine, cyano, $C_1$–$C_4$-alkoxy or $C_1$–$C_4$-alkoxy-carbonyl, represents $C_3$–$C_6$-alkenyloxy, represents di-($C_1$–$C_4$-alkyl)-amino, represents $C_3$–$C_6$-cycloalkyl, $C_3$–$C_6$-cycloalkylamino or $C_3$–$C_6$-cycloalkyl-$C_1$–$C_4$-alkyl, each of which is optionally substituted by fluorine, chlorine, bromine, cyano and/or $C_1$–$C_4$-alkyl, or represents phenyl or phenyl-$C_1$–$C_4$-alkyl, each of which is optionally substituted by fluorine, chlorine, bromine, cyano, nitro, $C_1$–$C_4$-alkyl, trifluoromethyl and/or $C_1$–$C_4$-alkoxy, $R^2$ represents hydrogen, hydroxyl, mercapto, amino, cyano, fluorine, chlorine, bromine, iodine, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents $C_2$–$C_6$-alkenyl or $C_2$–$C_6$-alkinyl, each of which is optionally substituted by fluorine, chlorine and/or bromine, represents $C_1$–$C_6$-alkoxy, $C_1$–$C_6$-alkylthio, $C_1$–$C_6$-alkylamino or $C_1$–$C_6$-alkyl-carbonylamino, each of which is optionally substituted by fluorine, chlorine, cyano, $C_1$–$C_4$-alkoxy or $C_1$–$C_4$-alkoxy-carbonyl, represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, represents di-($C_1$–$C_4$-alkyl)-amino, represents aziridino, pyrrolidino, piperidino or morpholino, each of which is optionally substituted by methyl and/or ethyl, represents $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio, or $C_1$–$C_4$-cycloalkyl-$C_1$–$C_4$-alkylamino, each of which is optionally substituted by fluorine, chlorine, bromine, cyano and/or $C_1$–$C_4$-alkyl, or represents phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, each of which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or $R^1$ and $R^2$ together represent optionally branched alkanediyl having 3 to 11 carbon atoms, furthermore, $R^3$, $R^4$ and $R^5$ are identical or different and each represents hydrocen, cyano, fluorine, chlorine, bromine, or represents alkyl, alkenyl, alkinyl, alkoxy, alkenyloxy, alkinyloxy, alkylthio, alkenylthio, alkinylthio, alkylsulphinyl or alkylsulphonyl, each of which has up to 6 carbon atoms and each of which is optionally substituted by fluorine, chlorine, bromine or $C_1$–$C_4$-alkoxy, or represents optionally cyano-, fluorine-, chlorine-, bromine- or $C_1$–$C_4$-alkyl-substituted cycloalkyl having 3 to 6 carbon atoms.

The invention furthermore preferably provides sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which A, J, Q and R each have the meanings given above as being preferred.

The invention in particular provides compounds of the formula (I) in which

A represents a single bond, represents oxygen, imino (NH), methylene ($CH_2$) or methylimino ($NCH_3$), J represents (hetero)aryl grouping selected from the series phenyl, pyridyl, pyrazolyl, thienyl, which is substituted by a 5,6-dihydro-[1,4,2]-dioxazin-3-yl group (formula below)

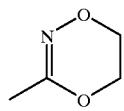

(which may for its part by substituted by fluorine, chlorine, methyl, ethyl or trifluoromethyl) and optionally by one or two further radicals selected from the series cyano, fluorine, chlorine, bromine, methyl, ethyl, n- or i-propyl, fluoromethyl, chloromethyl, difluoromethyl, dichloromethyl, trifluoromethyl, trichloromethyl, phenyl, pyridyl, Q represents oxygen or sulphur and R represents heterocyclyl, each of which is optionally substituted, of the formulae below

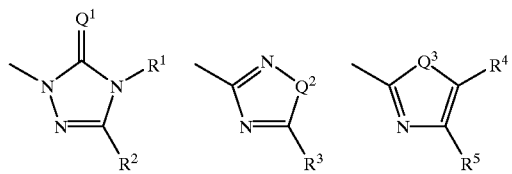

in which $Q^1$, $Q^2$ and $Q^3$ each represent oxygen or sulphur and $R^1$ represents hydrogen, hydroxyl, amino, represents methyl, ethyl, n- or i-propyl, n-, i-, s- or t-butyl, each of which is optionally substituted by fluorine, chlorine, cyano, methoxy or ethoxy, represents propenyl, butenyl, propinyl or butinyl, each of which is optionally substituted by fluorine, chlorine or bromine, represents methoxy, ethoxy. n- or i-propoxy, n-, i-, s- or t-butoxy, methylamino, ethylamino, n- or i-propylamino, n-, i-, s- or t-butylamino, each of which is optionally substituted by fluorine, chlorine, cyano, methoxy or ethoxy, represents propenyloxy or butenyloxy, represents dimethylamino or diethylamino, represents cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, each of which is optionally substituted by fluorine, chlorine, methyl and/or ethyl, or represents phenyl or benzyl, each of which is optionally substituted by fluorine, chlorine, methyl, trifluoromethyl and/or methoxy, $R^2$ represents hydrogen, hydroxyl, mercapto, amino, fluorine, chlorine, bromine, represents methyl, ethyl, n- or i-propyl, n-, i-, s- or t-butyl, each of which is optionally substituted by fluorine, chlorine, cyano, methoxy or ethoxy, represents ethenyl, propenyl, butenyl, propinyl or butinyl, each of which is optionally substituted by fluorine, chlorine or bromine, represents methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, each of which is optionally substituted by fluorine, chlorine, cyano, methoxy or ethoxy, represents propenyloxy, butenyloxy, propinyloxy, butinyloxy, propenylthio, propadienylthio butenylthio, propinylthio, butinylthio, propenylamino, butenylamino, propinylamino or butinylamino, represents dimethylamino, diethylamino or dipropylamino, represents cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, each of which is optionally substituted by fluorine, chlorine, methyl and/or ethyl, or represents phenyl, benzyl, phenoxy, benzyloxy, phenylthio, benzylthio, phenylamino or benzylamino, each of to which is optionally substituted by fluorine, chlorine, methyl, trifluoromethyl, methoxy and/or methoxycarbonyl, or $R^1$ and $R^2$ together represent optionally branched alkanediyl having 3 to 11 carbon atoms, furthermore, $R^3$, $R^4$ and $R^5$ are identical or different and each represents hydrogen, cyano, fluorine, chlorine, bromine, or represents methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylsulphinyl, ethylsulphinyl, methylsulphonyl or ethylsulphonyl, each of which is optionally substituted by fluorine, chlorine, methoxy or ethoxy, or represents cyclopropyl.

The abovementioned general or preferred radical definitions apply both to the end products of the formula (I) and, correspondingly, to the precursors or intermediates required in each case for the preparation. These radical definitions can be combined with one another as desired, thus including combinations between the preferred ranges indicated.

Using, for example, 2-(5,6-dihydro-[1,4,2]-dioxazin-3-yl)-6-fluoro-benzenesulphonamide and 5-ethoxy-4-methyl-2-phenoxycarbonyl-2,4-dihydro-3H-1,2,4-triazol-3-thione as starting materials, the course of the reaction in the process (a) according to the invention can be illustrated by the following scheme:

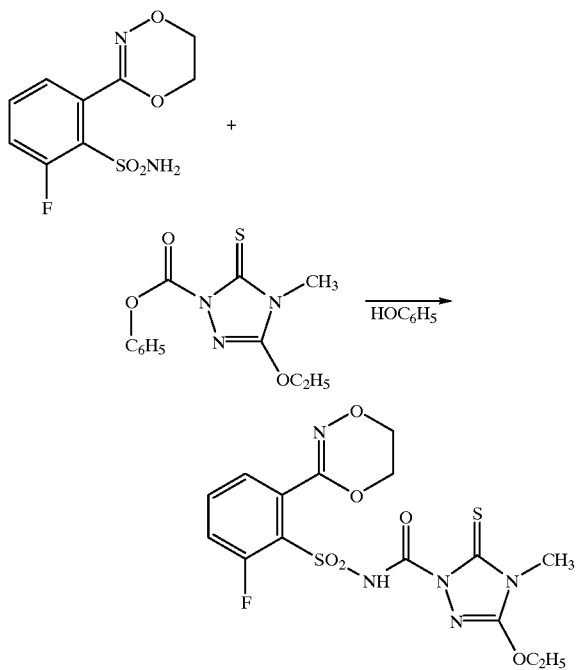

Using, for example, 4-chloro-2-(5,6-dihydro-[1,4,2]-dioxazin-3-yl)-3-thienylsulphonyl isothiocyanate and 5-ethyl-4-methoxy-2,4-dihydro-3H-1,2,4-triazol-3-one as starting materials, the course of the reaction in process (b) according to the invention can be illustrated by the following scheme:

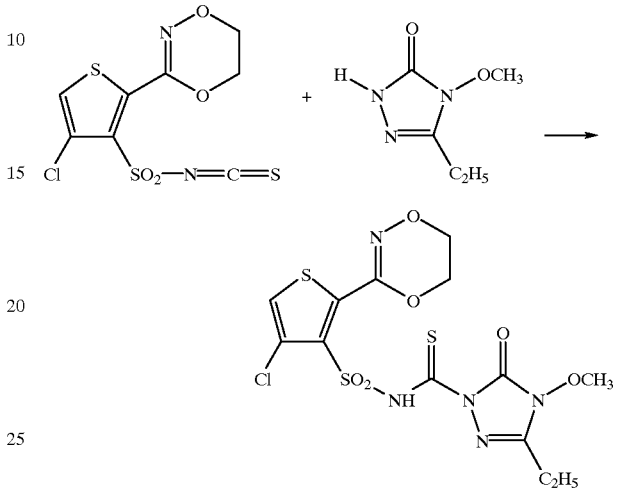

Using, for example, 3-(5,6-dihydro-[1,4,2]-dioxazin-3-yl)-pyridine-2-sulphonyl chloride, 5-ethylthio-4-methoxy-2,4-dihydro-3H-1,2,4-triazol-3-one and potassium cyanate as starting materials, the course of the reaction in the process (c) according to the invention can be illustrated by the following scheme:

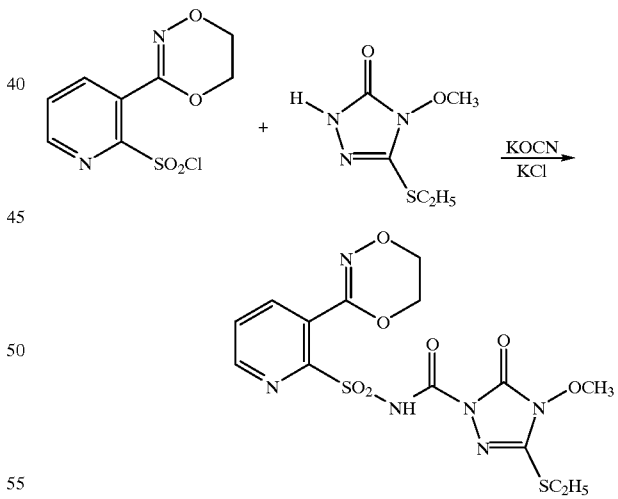

Using, for example, 2-(5,6-dihydro-[1,4,2]-dioxazin-3-yl)-6-trifluoro-methyl-benzenesulphonyl chloride and 5-methyl-1,2,4-oxadiazole-3-carboxamide as starting materials, the course of the reaction in the process (d) according to the invention can be illustrated by the following scheme:

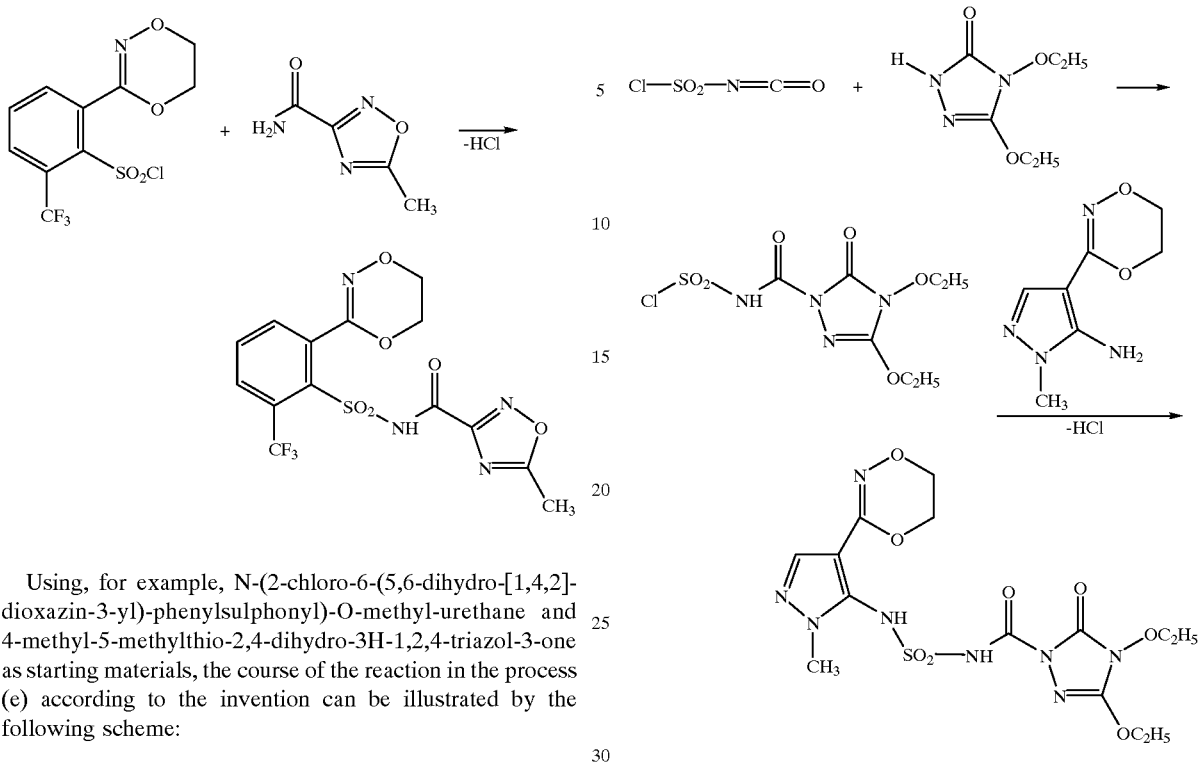

Using, for example, N-(2-chloro-6-(5,6-dihydro-[1,4,2]-dioxazin-3-yl)-phenylsulphonyl)-O-methyl-urethane and 4-methyl-5-methylthio-2,4-dihydro-3H-1,2,4-triazol-3-one as starting materials, the course of the reaction in the process (e) according to the invention can be illustrated by the following scheme:

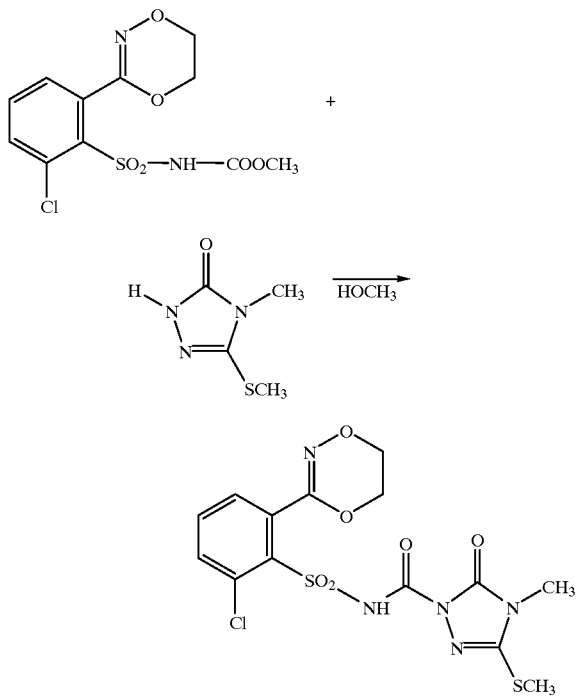

Using, for example, 4,5-diethoxy-2,4-dihydro-3H-1,2,4-triazol-3-one and chlorosulphonyl isocyanate and subsequently 5-amino-4-(5,6-dihydro-[1,4,2]-dioxazin-3-yl)-1-methyl-pyrazole as starting materials, the course of the reaction in the process (f) according to the invention can be illustrated by the following scheme:

The formula (II) provides a general definition of the aminosulphonyl compounds to be used as starting materials in the process (a) according to the invention for preparing the compounds of the formula (I). In the formula (II), A and J each preferably or in particular have those meanings which have already been indicated above, in connection with the description of the compounds of the formula (I) according to the invention. as being preferred or as being particularly preferred for A and J.

The starting materials of the formula (II) are known and/or can be prepared by known processes (cf. EP 645386, Preparation Examples). However, specific novel compounds of the formula (II) also form part of the subject-matter of this invention.

The formula (III) provides a general definition of the (thio)carboxylic acid derivatives further to be used as starting materials in the process (a) according to the invention for preparing the compounds of the formula (I). In the formula (III), Q and R each preferably or in particular have those meanings which have already been mentioned above, in connection with the description of the compounds of the formula (I) according to the invention, as being preferred or as being particularly preferred for Q and R; Z preferably represents fluorine, chlorine, bromine, $C_1$–$C_4$-alkoxy, phenoxy or benzyloxy, in particular represents chlorine, methoxy, ethoxy or phenoxy.

The starting materials of the formula (III) are known and/or can be prepared by processes known per se (cf. EP 459244, EP 341489, EP 422469, EP 425948, EP 431291, EP 507171, EP 534266).

The formula (IV) provides a general definition of the sulphonyl iso(thio)cyanates to be used as starting materials in the process (b) according to the invention for preparing the compounds of the formula (I). In the formula (IV), A, J and Q each preferably or in particular have those meanings which have already been mentioned above, in connection with the description of the compounds of the formula (I), as being preferred or as being particularly preferred for A, J and Q.

The starting materials of the formula (IV) are known and/or can be prepared by processes known per se (cf. EP 645386, Preparation Examples).

The formula (V) provides a general definition of the heterocycles to be used as starting materials in the processes (b), (c), (e) and (f) according to the invention for preparing the compounds of the formula (I). In the formula (V), R preferably or in particular has those meanings which have already been mentioned above, in connection with the description of the compounds of the formula (I) according to the invention, as being preferred or as being particularly preferred for R.

The starting materials of the formula (V) are known and/or can be prepared by known methods (cf. EP 341 489, EP 422 469, EP 425 948, EP 431 291, EP 507 171, EP 534 266).

The formula (IV) provides a general definition of the chlorosulphonyl compounds to be used as starting materials in the processes (c) and (d) according to the invention for preparing compounds of the formula (I). In the formula (IV), A and J each preferably or in particular have those meanings which have already been mentioned above, in connection with the description of the compounds of the formula (I) according to the invention, as being preferred or as being particularly preferred for A and J.

The starting materials of the formula (IV) are known and/or can be prepared by processes known per se (cf. EP 645386, Preparation Examples).

The formula (VIII) provides a general definition of the (thio)carboxamides to be used as starting materials in the process (d) according to the invention for preparing the compounds of the formula (I). In the formula (VIII), Q and R each preferably or in particular have those meanings which have already been mentioned above, in connection with the description of the compounds of the formula (I) according to the invention, as being preferred or as being particularly preferred for Q and R.

The starting materials of the formula (VIII) are known and/or can be prepared by processes known per se (cf. EP 459 244).

The formula (IX) provides a general definition of the sulphonylamino(thio)carbonyl compounds to be used as starting materials in the process (e) according to the invention for preparing the compounds of the formula (I). In the formula (IX), A, J and Q each preferably or in particular have those meanings which have already been mentioned above, in connection with the description of the compounds of the formula (I) according to the invention, as being preferred or as being particularly preferred for A, J and Q; Z preferably represents fluorine, chlorine, bromine, $C_1$–$C_4$-alkoxy, phenoxy or benzyloxy, in particular represents chlorine, methoxy, ethoxy or phenoxy.

The starting materials of the formula (IX) are known and/or can be prepared by processes known per se.

The formula (XI) provides a general definition of the (hetero)aryl compounds to be used as starting materials in the process (f) according to the invention for preparing compounds of the formula (I). In the formula (XI), A and J each preferably or in particular have those meanings which have already been mentioned above, in connection with the description of the compounds of the formula (I) according to the invention, as being preferred or as being particularly preferred for A and J.

The starting materials of the formula (XI) are known and/or can be prepared by processes known per se (cf. WO 94/08979).

The processes (a), (b), (c), (d), (e) and (f) according to the invention for preparing the novel compounds of the formula (I) are preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers such as diethyl and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles, such as, for example, acetonitrile and propionitrile; amides such as, for example, dimethylformamide, dimethylacetamide and N-methylpyrrolidone and also dimethylsulphoxide, tetramethylene sulphone and hexamethylphosphoric triamide.

As reaction auxiliaries and/or as acid acceptors in the processes (a), (b), (c), (d), (e) and (f) according to the invention it is possible to employ all acid-binding agents which can customarily be used for such reactions. Preference is given to alkali metal hydroxides, for example sodium hydroxide and potassium hydroxide, alkaline earth metal hydroxides, for example calcium hydroxide, alkali metal carbonates and alkoxides, such as sodium carbonate and potassium carbonate, sodium tert-butoxide and potassium tert-butoxide, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures in the processes (a), (b), (c), (d), (e) and (f) according to the invention can be varied within a relatively wide range. The reactions are in general carried out at temperatures of between −20° C. and +150° C., preferably at temperatures between 0° C. and +100° C.

The processes (a), (b), (c), (d), (e) and (f) according to the invention are generally carried out under atmospheric pressure. However, it is also possible to operate under elevated or reduced pressure.

For carrying out the processes (a), (b), (c), (d), (e) and (f) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c), (d) and (e) according to the invention is in each case carried out by customary methods (cf. the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial crops, for example forests, decorative tree plantings, orchards, vineyards, citrus groves, nut orchards, banana plantations, coffee plantations. tea plantations, rubber plantations, oil palm plantations, cocoa plantations, soft fruit plantings and hopfields, in lawns, turf and pastureland, and for the selective control of weeds in annual crops.

The compounds of the formula (I) according to the invention are particularly suitable for the selective control of monocotyledonous and dicotyledonous weeds in monocotyledonous and dicotyledonous crops, both pre-emergence and post-emeraence.

To a certain extent, the compounds of the formula (I) also have fungicidal activity, for example against Pyricularia oryzae in rice.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ for example organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general comprise between 0.1 and 95 per cent by weight of active compound, preferably between 0.5 and 90%.

For controlling weeds, the active compounds according to the invention, as such or in the form of their formulations, can also be used as mixtures with known herbicides, ready-to-use formulations or tank mixes being possible.

Possible components for the mixtures are known herbicides, for example anilides, such as, for example, diflufenican and propanil; arylcarboxylic acids, such as, for example, dichloropicolinic acid, dicamba and picloram; aryloxyalkanoic acids, such as, for example, 2,4-D, 2,4-DB, 2,4-DP, fluroxypyr, MCPA, MCPP and triclopyr; aryloxyphenoxy-alkanoic esters, such as, for example, diclofop-methyl, fenoxaprop-ethyl, fluazifop-butyl, haloxyfop-methyl and quizalofop-ethyl; azinones, such as, for example, chloridazon and norflurazon; carbamates, such as, for example, chlorpropham, desmedipham, phenmedipham and propham; chloroacetanilides, such as, for example, alachlor, acetochlor, butachlor, metazachlor, metolachlor, pretilachlor and propachlor; dinitroanilines, such as, for example, oryzalin, pendimethalin and trifluralin; diphenyl ethers, such as, for example, acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as, for example, alloxydim, clethodim, cycloxydim, sethoxydim and tralkoxydim; imidazolinones, such as, for example, imazethapyr, imazamethabenz, imazapyr and imazaquin; nitriles, such as, for example, bromoxynil, dichlobenil and ioxynil; oxyacetamides, such as mefenacet; sulphonyl-ureas, such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as, for example, butylate, cycloate, diallate, EPTC, esprocarb, molinate, prosulfocarb, thiobencarb and triallate; triazines, such as, for example, atrazine, cyanazine, simazine, simetryne, terbutryne and terbutylazine; triazinones, such as, for example, hexazinone, metamitron and metribuzin; others, such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

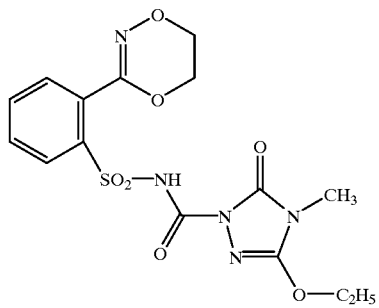

(Process (a))

A mixture of 2.6 g (10 mmol) of 5-ethoxy-4-methyl-2-phenoxycarbonyl-2,4-dihydro-3H-1,2,4-triazol-3-one, 2,4 g (10 mmol) of 2-(5,6-dihydro-[1,4,2]-dioxazin-3-yl)-benzenesulphonamide, 1,6 g (10 mmol) of 1,8-diazabicyclo-[5,4,0]-undec-7-ene (DBU) and 20 ml of acetonitrile is stirred at room temperature (approximately 20° C.) for about 60 minutes. The mixture is then diluted with approximately the same parts by volume of methylene chloride and water to about three times its volume and slightly acidified using 1N hydrochloric acid (pH ~3). The organic phase is separated off, dried with sodium sulphate and filtered. The filtrate is concentrated, the residue is digested with diethyl ether and the resulting crystalline product is isolated by filtration with suction.

This gives 2.1 g (51% of theory) of 5-ethoxy-4-methyl-2-(2-(5,6-dihydro-[1,4,2]-dioxazin-3-yl)-phenylsulphonylaminocarbonyl)-2,4-dihydro-3H1,2,4-triazol-3-one of melting point 173° C.

Similar to Example 1, and in accordance with the general description of the preparation processes according to the invention, it is also possible to prepare, for example, the compounds of the formula (I) listed in Table 1 below.

TABLE 1

Examples of compounds of the formula (I)

| Ex. No. | A | J | Q | R | Melting point (° C.) |
|---|---|---|---|---|---|
| 2 | — | | O | | 131 |

TABLE 1-continued

Examples of compounds of the formula (I)

| Ex. No. | A | J | Q | R | Melting point (° C.) |
|---|---|---|---|---|---|
| 3 | — | 2-methylphenyl-substituted 1,3,4-dioxazine | O | 1,4-dimethyl-5-(n-propoxy)-1,2,4-triazol-3(4H)-one | 144 |
| 4 | — | 2-methylphenyl-substituted 1,3,4-dioxazine | O | 1,4-dimethyl-5-(methylthio)-1,2,4-triazol-3(4H)-one | 165 |
| 5 | — | 2-methylphenyl-substituted 1,3,4-dioxazine | O | 5-ethyl-1,4-dimethyl-1,2,4-triazol-3(4H)-one | 146 |
| 6 | — | (1,5-dimethylpyrazol-4-yl)-substituted 1,3,4-dioxazine | O | 1,4-dimethyl-5-(methylthio)-1,2,4-triazol-3(4H)-one | 198 |
| 7 | — | (1,5-dimethylpyrazol-4-yl)-substituted 1,3,4-dioxazine | O | 5-ethyl-1,4-dimethyl-1,2,4-triazol-3(4H)-one | 153 |
| 8 | — | (1,5-dimethylpyrazol-4-yl)-substituted 1,3,4-dioxazine | O | 5-ethoxy-1,4-dimethyl-1,2,4-triazol-3(4H)-one | 207 |
| 9 | — | oxime ether | O | acetyl CH₃ | 187 |

Starting Materials of the Formula (II):

Example (II-1)

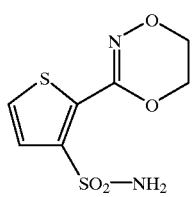

20.15 g (0.29 mol) of hydroxylammonium chloride are initially charged in 350 ml of methanol, and a solution of 32.5 g (0.58 mol) of potassium hydroxide powder in 150 ml of methanol is added dropwise. 32.0 g (0.145 mol) of 2-methoxycarbonyl-thiophene-3-sulphonamide are subsequently added, a little at a time, to this solution. The reaction mixture is then stirred at approximately 40° C. for about 15 hours. 20 g (0.145 mol) of potassium carbonate are then added and 89.9 g (0.48 mol) of 1,2-dibromo-ethane are added dropwise, and the reaction mixture is stirred at approximately 60° C. for a further 15 hours. The mixture is concentrated under water pump vacuum and the residue is then stirred with water, neutralized with sodium dihydrogen phosphate and shaken with methylene chloride. The organic phase is dried with sodium sulphate and filtered. The filtrate is concentrated under water pump vacuum, the residue is digested with ethyl acetate and the crystalline product is isolated by filtration with suction.

This gives 10.6 g (29.5% of theory) of 2-(5,6-dihydro-[1,4,2]-dioxazin-3-yl)-thiophene-3-sulphonamide of melting point 180° C.

Example (II-2)

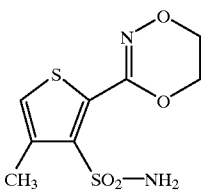

Step 1

With heating, 62.9 g (0.90 mol) of hydroxylammonium chloride are dissolved in 600 ml of methanol, and a solution of 101 g (1.80 mol) of potassium hydroxide in 600 ml of methanol is added at room temperature (approximately 20° C.). 106 g (0.45 mol) of methyl 3-bromo-4-methyl-thiophene-2-carboxylate are subsequently metered in a little at a time, and the reaction mixture is then stirred at 40° C. for 3 hours. 381 g (2.03 mol) of 1,2-dibromo-ethane and 62.3 g (0.45 mol) of potassium carbonate are added, and the mixture is then heated under reflux for approximately 90 minutes. A further 169.5 g (0.90 mol) of 1,2-dibromo-ethane and a further 62.3 g (0.45 mol) of potassium carbonate are then added, and the mixture is heated under reflux for a further 3 hours. After cooling to room temperature, the mixture is filtered off with suction, the filtrate is concentrated under water pump vacuum and the residue is shaken with methylene chloride/water. The organic phase is separated off, dried with magnesium sulphate and filtered. The filtrate is concentrated using water pump vacuum and the residue is then purified by column chromatography (silica gel, ethyl acetate/cyclohexane: 1:15 to 1:3).

This gives 32.8 g (28% of theory) of 2-(5,6-dihydro-[1,4,2]-dioxazin-3-yl)-3-bromo-4-methyl-thiophene of melting point 67° C.

Step 2

At –100° C., a solution of 786 mg (3.0 mmol) of 2-(5,6-dihydro-[1,4,2]-dioxazin-3-yl)-3-bromo-4-methyl-thiophene in 30 ml of tetrahydrofuran is admixed with 1.44 ml of n-butyllithium (2.5 M in hexane). The mixture is stirred at –70° C. for 10 minutes; sulphur dioxide is then introduced. The mixture is allowed to warm to room temperature (approximately 20° C.), 50 ml of hexane are added and the mixture is filtered off with suction. The lithium salt of 2-(5,6-dihydro-[1,4,2]-dioxazin-3-yl)-4-methyl-thiophene-3-sulphinic acid, which is obtained as a solid product, is employed for the next step without further purification.

Step 3

A lithium salt of 2-(5,6-dihydro-[1,4,2]-dioxazin-3-yl)-4-methyl-thiophene-3-sulphinic acid obtained according to step 2 is taken up in 30 ml of water/30 ml of methylene chloride, and 0.82 g (60 mmol) of N-chloro-succinimide are added at approximately 10° C. The mixture is stirred for approximately 15 minutes; the organic phase is then separated off and the aqueous phase is reextracted three times with methylene chloride; the combined organic phases are washed with 5% strength sodium hydrogen sulphite solution, dried with magnesium sulphate and filtered. This gives a virtually anhydrous solution of 2-(5,6-dihydro-[1,4,2]-dioxazin-3-yl)-4-methyl-thiophene-3-sulphonyl chloride.

Step 4

At –40° C., ammonia is introduced into the solution obtained according to step 3. The mixture is then allowed to warm to room temperature (approximately 20° C.) and filtered off with suction, and the filtrate is concentrated under water pump vacuum.

This gives 0.58 g (74% of theory) of 2-(5,6-dihydro-[1,4,2]-dioxazin-3-yl)-4-methyl-thiophene-3-sulphonamide of melting point 155° C.

This product has not yet been disclosed in the literature and, as a novel compound, also forms part of the subject-matter of the present application.

Example (II-3)

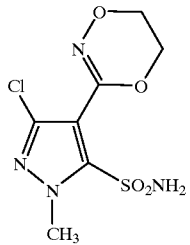

Step 1

With heating, 24.3 g (0.35 mol) of hydroxylammonium chloride are dissolved in 240 ml of methanol and, at room temperature (approximately 20° C.), the mixture is admixed with a solution of 39.3 g (0.70 mol) of potassium hydroxide in 240 ml of methanol. 33.0 g (0.175 mol) of ethyl 1-methyl-3-chloro-pyrazole-4-carboxylate are subsequently introduced, and the reaction mixture is stirred at 40° C. for about one hour. 148 g (0.79 mol) of 1,2-dibromo-ethane and 24.2 g (0.175 mol) of potassium carbonate are added, and the mixture is then heated under reflux for about one hour. A further 32.9 g (27.5 mmol) of 1,2-dibromo-ethane and a further 6.05 g (44 mmol) of potassium carbonate are then added, and the mixture is heated under reflux for a further 30 minutes. The mixture is then allowed to cool and filtered off with suction, and the filtrate is concentrated under water pump vacuum. The residue is shaken with methylene chloride/water and the organic phase is separated off, dried with magnesium sulphate and filtered. The filtrate is concentrated and the residue is recrystallized from ethyl acetate/cyclohexane (1:1).

This gives 17.8 g (50.5% of theory) of 4-(5,6-dihydro-[1,4,2]-dioxazin-3-yl)-3-chloro-1-methyl-pyrazole of melting point 112° C.

Step 2

At −70° C., 32 ml of n-butyllithium (2.5 M in hexane) are added dropwise to a solution of 7.78 g (77 mmol) of diisopropylamine in 40 ml of diethyl ether. At −70° C., the resulting solution is then added dropwise to a solution of 10.1 g (0.05 mol) of 4-(5,6-dihydro-[1,4,2]-dioxazin-3-yl)-3-chloro-1-methyl-pyrazole in 100 ml of diethyl ether. The mixture is stirred at −70° C. for 1 hour. Sulphur dioxide is then introduced, the mixture is allowed to warm to room temperature (approximately 20° C.) and the intermediate—the lithium salt of 4-(5,6-dihydro-[1,4,2]-dioxazin-3-yl)-3-chloro-1-methyl-pyrazole-sulphinic acid—is then isolated by filtration with suction.

Step 3

The intermediate according to step 2 is taken up in 80 ml of water/80 ml of methylene chloride, and 12 g (90 mmol) of N-chloro-succinimide are metered in a little at a time at 0° C. The mixture is stirred at 0° C. for about 15 minutes. The phases are then separated and the aqueous phase is reextracted three times with methylene chloride. The combined organic phases are washed with 5% strength sodium hydrogen sulphite solution, dried with magnesium sulphate and filtered. This gives a virtually anhydrous solution of 4-(5,6-dihydro-[1,4,2]-dioxazin-3-yl)-3-chloro-1-methyl-pyrazole-5-sulphonyl chloride.

Step 4

At −40° C., ammonia is introduced into the solution obtained according to step 3. The mixture is then allowed to warm to room temperature (approximately 20° C.) and filtered off with suction, and the filtrate is concentrated under water pump vacuum. The crude product which is obtained as the residue is purified by column chromatography (silica gel, ethyl acetate/cyclohexane 1:1).

This gives 2.5 g (12% of theory) of 4-(5,6-dihydro-[1,4,2]-dioxazin-3-yl)-3-chloro-1-methyl-pyrazole-5-sulphonamide of melting point 158° C.

This product has not yet been disclosed in the literature and, as a novel compound, also forms part of the subject-matter of the present application. This also applies to the compounds mentioned below.

Similarly to Examples (II-1) to (II-3), it is also possible to prepare, for example, the following compounds of the formula (II):

Example (II-4)

4-(5,6-dihydro-[1,4,2]-dioxazin-3-yl)-1,3-dimethyl-pyrazole-5-sulphonamide (novel compound of melting point 145° C.).

Example (II-5)

4-(5,6-dihydro-[1,4,2]-dioxazin-3-yl)-1-phenyl-pyrazole-5-sulphonamide (novel compound of melting point 116° C).

Example (II-6)

4-(5,6-dihydro-[1,4,2]-dioxazin-3-yl)-1-(pyridin-2-yl)-pyrazole-5-sulphonamide (novel compound of melting point 141° C.).

USE EXAMPLES

Example A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound in such a way as to apply the particular amounts of active compound desired per unit area. The concentration in the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example the compounds of Preparation Examples 1, 3 and 4 exhibit very strong activity against weeds, while being substantially competitive with crop plants, such as, for example, wheat, soya and cotton (cf. Table A).

TABLE A

Pre-emergence test/greenhouse

| Active compound | Application rate (g of ai./ha) | Soya | Avena fatua | Bromus | Poa | Galin-soga | Matri-caria | Viola |
|---|---|---|---|---|---|---|---|---|

TABLE A-continued

| Active compound | Application rate (g of ai./ha) | Wheat | Cotton | Avena fatua | Bromus | Poa | Galin-soga | Matri-caria | Viola |
|---|---|---|---|---|---|---|---|---|---|
| (3) [structure: benzene with N-O-CH₂-CH₂-O dioxazine ring, SO₂—NH—C(O)—N-triazolinone with N-CH₃ and O—CH₂—CH₂—CH₃] | 125 | 10 | 90 | 90 | 95 | 80 | 90 | 95 |
| (1) [structure: benzene with N-O-CH₂-CH₂-O dioxazine ring, SO₂—NH—C(O)—N-triazolinone with N-CH₃ and O—C₂H₅] | 125 | 0 | 95 | 90 | 95 | 95 | 95 | 70 |
| (4) [structure: benzene with N-O-CH₂-CH₂-O dioxazine ring, SO₂—NH—C(O)—N-triazolinone with N-CH₃ and S—CH₃] | 125 | 10 | 0 | 95 | 90 | 95 | 100 | 95 | 90 |

Example B
Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration in the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example the compounds of Preparation Examples 1, 4 and 11 exhibit strong activity against weeds (cf. Table B).

TABLE B

Post-emergence test/greenhouse

| Active compound | Application rate (g of ai./ha) | Avena fatua | Echino-chloa | Galium | Poly gonum | Viola |
|---|---|---|---|---|---|---|
| (4) | 125 | 80 | 90 | 95 | 80 | 80 |
| (1) | 60 | 80 | 90 | 90 | 90 | 90 |
| (11) | 250 | 60 | 80 | 90 | 90 | 90 |

What is claimed is:

1. A substituted sulphonylamino(thio)carbonyl compound of the formula (I)

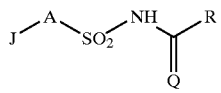

wherein

A represents a single bond, oxygen, imino, $C_1$–$C_4$-alkanediyl or $C_1$–$C_4$-alkylimino;

J represents a heteroaryl grouping selected from the series consisting of phenyl, pyridyl, pyrazolyl and thienyl which is substituted by a 5,6-dihydro-1,4,2-dioxazin-3-yl group which is unsubstituted or substituted by halogen, $C_1$–$C_4$-alkyl or $C_1$–$C_4$-halogenoalkyl and by zero to two additional substituents selected from the group consisting of cyano, halogen, $C_1$–$C_4$-alkyl, $C_1$–$C_4$-halogenoalkyl, phenyl, and pyridyl;

Q represents oxygen or sulphur and

R represents a heterocyclyl of the following formula

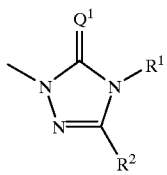

wherein $Q^1$ represents oxygen or sulphur and $R^1$ represents hydrogen; hydroxyl; amino; cyano; $C_2$–$C_{10}$-alkylideneamino; unsubstituted or fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl; $C_2$–$C_6$-alkenyl or $C_2$–$C_6$- alkinyl, each of which is unsubstituted or substituted by halogen selected from the group consisting of fluorine, chlorine and bromine; $C_1$–$C_6$-alkoxy, $C_1$–$C_6$-alkylamino or $C_1$–$C_6$-alkyl-carbonylamino, each of which is unsubstituted or substituted by fluorine, chlorine, bromine, cyano, $C_1$–$C_4$-alkoxy or $C_1$–$C_4$-alkoxy-carbonyl; $C_3$–$C_6$-alkenyloxy; di-($C_1$-$C_4$-alkyl)-amino; $C_3$–$C_6$-cycloalkyl, $C_3$–$C_6$-cycloalkylamino or $C_3$–$C_6$-cycloalkyl-$C_1$–$C_4$-alkyl, each of which is unsubstituted or substituted by a substituent selected from the group consisting of fluorine, chlorine, bromine, cyano and $C_1$–$C_4$-alkyl; phenyl or phenyl-$C_1$–$C_4$alkyl, each of which is unsubstituted or substituted by a substituent selected from the group consisting of fluorine, chlorine, bromine, cyano, nitro, $C_1$–$C_4$-alkyl, trifluoromethyl and $C_1$–$C_4$-alkoxy;

$R^2$ represents hydrogen; hydroxyl; mercapto; amino; cyano; fluorine; chlorine; bromine; iodine; unsubstituted or fluorine-chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl; $C_2$–$C_6$-alkenyl or $C_2$–$C_6$-alkinyl, each of which is unsubstituted or substituted by halogen selected from the group consisting of fluorine, chlorine and bromine; $C_1$–$C_6$-alkoxy, $C_3$–$C_6$-alkylthio, $C_3$–$C_6$-alkylamino or $C_1$–$C_6$-alkyl-carbonylamino, each of which is unsubstituted or substituted by fluorine, chlorine, cyano, $C_1$–$C_4$-alkoxy or $C_1$–$C_4$-alkoxy-carbonyl; $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino; di-($C_1$–$C_4$-alkyl)-amino; aziridino, pyrrolidino, piperidino or morpholino, each of which is unsubstituted or substituted by alkyl selected from the group consisting of methyl and ethyl; $C_3$–$C_6$-cycloalkyl, $C_3$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio, or $C_3$–$C_6$-cycloalkyl-$C_1$–$C_4$-alkylamino, each of which is unsubstituted or substituted by a substituent selected from the group consisting of fluorine, chlorine, bromine, cyano and $C_1$–$C_4$-alkyl; phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, each of which is unsubstituted or substituted by a substituent selected from the group consisting of fluorine, chlorine, bromine, cyano, nitro, $C_1$–$C_4$-alkyl, trifluoromethyl, $C_1$–$C_4$-alkoxy and $C_1$–$C_4$-alkoxy-carbonyl; or $R^1$ and $R^2$ together represent unbranched or branched alkanediyl having from 3 to 11 carbon atoms, and/or a salt of said compound, said salt being selected from the group consisting of a sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts.

2. The compound of claim 1, wherein

A represents a single bond, oxygen, imino, methylene or methylimino,

J represents a heteroaryl grouping selected from the series consisting of phenyl, pyridyl, pyrazolyl, thienyl, which is substituted by a 5,6-dihydro-1,4,2-dioxazin-3-yl group of the formula:

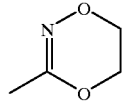

which is unsubstituted or substituted by fluorine, chlorine, methyl, ethyl or trifluoromethyl and by zero to two additional substituents selected from the group consisting of cyano, fluorine, chlorine, bromine, methyl, ethyl, n- or i-propyl, fluoromethyl, chloromethyl, difluoromethyl, dichloromethyl, trifluromethyl, trichloromethyl, phenyl, and pyridyl;

Q represents oxygen or sulphur and

R represents the heterocyclyl of the formula:

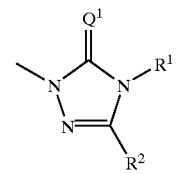

wherein $Q^1$ represents oxygen or sulphur and $R^1$ represents hydrogen; hydroxyl; amino; methyl, ethyl, n- or i-propyl, n-, i-, s- or t-butyl, each of which is unsubstituted or substituted by fluorine, chlorine, cyano, methoxy or ethoxy; propenyl, butenyl, propinyl or butinyl, each of which is unsubstituted or substituted by fluorine, chlorine or bromine; methoxy, ethoxy, n- or i-propoxy, n-, i-, s- or t-butoxy, methylamino, ethylamino, n- or i-propylamino, n-, i-, s- or t-butylamino, each of which is unsubstituted or substituted by fluorine, chlorine, cyano, methoxy or ethoxy; propenyloxy or butenyloxy; dimethylamino or diethylamino; cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, each of which is unsubstituted or substituted by a substituent selected from the group consisting of fluorine, chlorine, methyl and ethyl; or, phenyl or benzyl, each of which is unsubstituted or substituted by a substituent selected from the group consisting of fluorine, chlorine, methyl, trifluoromethyl and methoxy;

$R^2$ represents hydrogen; hydroxyl; mercapto; amino; fluorine; chlorine; bromine; methyl, ethyl, n- or i-propyl, n-, i-, s- or t-butyl, each of which is unsubstituted or substituted by fluorine, chlorine, cyano, methoxy or ethoxy; ethenyl, propenyl, butenyl, propinyl or butinyl, each of which is unsubstituted or substituted by fluorine, chlorine or bromine; methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, each of which is unsubstituted or substituted by fluorine, chlorine, cyano, methoxy or ethoxy; propenyloxy, butenyloxy, propinyloxy, butinyloxy, propenylthio, propadienylthio, butenylthio, propinylthio, butinylthio, propenylamino, butenylamino, propinylamino or butinylamino; dimethylamino, diethylamino or dipropylamino; cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentyl methyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, each of which is unsubstituted or substituted by a substituent selected from the group consisting of fluorine, chlorine, methyl and ethyl; or, phenyl, benzyl, phenoxy, benzyloxy, phenylthio, benzylthio, phenylamino or benzylamino, each of which is unsubstituted or substituted by a substituent selected from the group consisting of fluorine, chlorine, methyl, trifluoromethyl, methoxy and methoxycarbonyl, or $R^1$ and $R^2$ together represent unbranched or branched alkanediyl having 3 to 11 carbon atoms.

3. A substituted sulphonylamino(thio)carbonyl compound of the formula

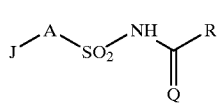 (I)

wherein

A represents a single bond,

J represents the following group

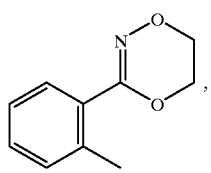,

Q represents oxygen,

R represents the following group

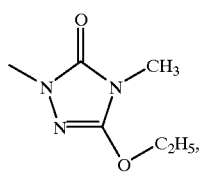

or a salt thereof.

4. The aminosulphonyl compound: 2-(5,6-dihydro-1,4,2-dioxazin-3-yl)-4-methyl-thiophene-3-sulphonamide.

5. A process for preparing a compound of the formula (I) according to claim 1 or a salt thereof, comprising the step of:

(a) reacting an aminosulphonyl compound of the general formula (II)

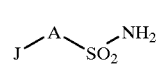 (II)

wherein

A and J are each as defined in claim 1, with a (thio)carboxylic acid derivative of the general formula (III)

 (III)

wherein

Q and R are each as defined in claim 1, and

Z represents a halogen, an alkoxy, an aryloxy or an arylalkoxy, or (b) reacting a sulphonyl iso(thio)cyanate of the general formula (IV)

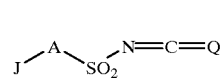 (IV)

wherein

A, J and Q are each as defined above, with a heterocycle of the general formula (V)

H—R (V)

wherein

R is as defined above, or (c) reacting a chlorosulphonyl compound of the general formula (VI)

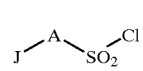 (VI)

wherein

A and J are each as defined above, with a heterocycle of the general formula (V)

H—R (V)

wherein

R is as defined above, and a metal(thio)cyanate of the general formula (VII)

MQCN (VII)

wherein

Q is as defined above, and

M represents an alkali metal or alkaline earth metal equivalent, or (d) reacting a chlorosulphonyl compound of the general formula (VI)

(VI)

wherein
A and J are each as defined above,
with a (thio)carboxamide of the general formula (VII)

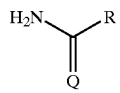
(VIII)

wherein
Q and R are each as defined above, or (e) reacting a sulphonylamino(thio)carbonyl compound of the general formula (IX)

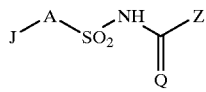
(IX)

wherein
A, J and Q are each as defined above, and
Z represents a halogen, an alkoxy, an aryloxy or an arylalkoxy,
with a heterocycle of the general formula (V)

 (V)

wherein
R is as defined above, or (f) reacting a heterocycle of the general formula (V)

 (V)

wherein
R is as defined above, with a chlorosulphonyl iso(thio)cyanate, to produce an adduct of the general formula (X)

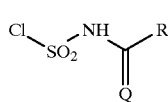
(X)

wherein
Q and R are each as defined above, and
reacting the adduct of the formula (X) in situ with a heteroaryl compound of the general formula (XI)

(XI)

wherein
A and J are each as defined above.

6. The process of claim 5 wherein steps a) d), e), and f) are carried out in the presence of an acid acceptor and a diluent.

7. The process of claim 5 wherein steps b) and c) are carried out in the presence of a reaction auxiliary and a diluent.

8. The process of claim 5 further comprising the step of converting the compound of the formula (I) obtained by process a), b), c), d), e), or f, into a salt thereof by customary methods.

9. A herbicidal composition comprising at least one compound of the formula (I) or a salt thereof according to claim 1 and one or more extenders and/or surfactants.

10. A method for controlling weeds comprising the step of allowing a compound of the general formula (I) or a salt thereof according to claim 1 to act on the weeds or their habitat.

11. A process for preparing a herbicidal composition comprising the step of mixing a compound of the general formula (I) or a salt thereof according to claim 1 with extenders and/or surfactants.

* * * * *